United States Patent [19]

Suhre

[11] Patent Number: 4,617,919
[45] Date of Patent: Oct. 21, 1986

[54] WHEELCHAIR WITH POSTURE SUPPORTS

[75] Inventor: Robert B. Suhre, Lakeville, Minn.

[73] Assignee: Theradyne Corporation, Lakeville, Minn.

[21] Appl. No.: 529,517

[22] Filed: Sep. 6, 1983

[51] Int. Cl.[4] ............................................... A61F 5/02
[52] U.S. Cl. ............................ 128/78; 280/289 WC; 128/134
[58] Field of Search ............... 128/134, 78; 180/907; 297/DIG. 4; 280/289 WC

[56] References Cited

U.S. PATENT DOCUMENTS

| Re. 30,867 | 2/1982 | Gaffney | 297/DIG. 4 |
|---|---|---|---|
| 41,548 | 2/1864 | Taylor | 128/78 |
| 170,655 | 12/1875 | Allen | 128/78 |
| 951,560 | 3/1910 | Eaton | 128/78 |
| 3,635,526 | 1/1972 | Posey | 297/DIG. 4 |

FOREIGN PATENT DOCUMENTS

| 171892 | 12/1904 | Fed. Rep. of Germany | 128/78 |
|---|---|---|---|
| 2148248 | 9/1971 | Fed. Rep. of Germany | 128/78 |

*Primary Examiner*—Gene Mancene
*Assistant Examiner*—Wenceslao J. Contreras
*Attorney, Agent, or Firm*—Orrin M. Haugen; Thomas J. Nikolai; Frederick W. Niebuhr

[57] ABSTRACT

A wheelchair having a plurality of posture supports for adjustably supporting the neck, thoracic cavity and thighs. Each of the supports is independently and three dimensionally adjustable so as therapeutically support a wheelchair bound individual. The various supports are adjustable via a plurality of rods and set screw bound cylindrical couplers.

13 Claims, 9 Drawing Figures

WHEELCHAIR WITH POSTURE SUPPORTS

BACKGROUND OF THE INVENTION

The present invention generally relates to wheelchairs and in particular to an improved wheelchair having adjustable apparatus for supporting a seated individual in the wheelchair.

Many wheelchair-bound patients suffer from various muscular or skeletal disabilities which affect their posture. These disabilities may prevent such patients from sitting comfortably and therapeutically correct within a conventional wheelchair for any extended period of time. Poor posture may also have an adverse impact upon the patient's breathing, digestion, and general awareness. Conventional wheelchairs do not provide means to support such patients in an appropriate posture. Typically, most readily available wheelchairs provide no posture support. Support for the body's trunk is essential for individuals afflicted with skeletal conditions such as scoliosis, muscular conditions such as multiple sclerosis or muscular distrophy, or even nervous disorders such as cerebral palsy. Individuals affected by such disorders often require supports that contact the body trunk and upper shoulder area and and apply counteracting forces to those portions of the body trunk that are misaligned or otherwise in need of support to therapeutically maintain. Such supports are generally not present on wheelchairs sold commercially today.

While various designs have been known for providing some adjustable positioning support, such designs are not readily compatible with current wheelchair designs which stress lightness and durability. These prior support designs tend to be (1) complex in construction, (2) uncomfortable, (3) hamper movement into and out of the chair, (4) interfere with quick disassembly of the chair, and (5) difficult to align and secure in place.

Examples of such known supports used in connection with wheelchairs are described in U.S. Pat. No. 3,815,586, as well as the literature related to the Medical Equipment Distributors, Inc. (MED-STS spherical thoracic supports), page 112, among others, of *The Wheelchair Book* by H. L. Kamenentz (1969, Charles C. Thomas), and U.S. Pat. No. 3,764,180.

U.S. Pat. No. 3,815,586 generally discloses vertically and horizontally adjustable supports that mount to the arms of the wheelchair. The MED-STS publication discloses a variety of supports employing "ball" joints which are permanently mounted to the tubular side members of the back of the chair. *The Wheelchair Book* reference discloses an apparatus containing separate horizontally and vertically adjustable pads for obtaining back support which is intended to be inserted and strapped to the back of the wheelchair.

U.S. Pat. No. 3,764,180 discloses a horizontally adjustable yoke-like neck support which includes attendant shoulder pads. This neck support, however, is neither vertically nor tiltably adjustable.

The present invention, like the above assemblies, employs independently adjustable posture pads for applying supporting and counteracting forces to the body of a seated individual. Specifically included are a neck support, shoulder pads, trunk support pads and thigh pads. The neck support is adjustable horizontally, vertically and radially. The shoulder pads are swivably mounted along the right and left side. The distance between the pad and the back of the chair is also adjustable. The truck support pads, mounted on the adjustable height arms of the chair, are adjustable inwardly and outwardly from the center of the chair as well as inwardly and outwardly from the back of the chair to accommodate patients having differing hip posturing demands. The thigh support is retractably mounted to the base of the seat.

Since the supports are all vertically, horizontally and radially adjustable, the present invention permits a tailored adjustment to provide maximum support and comfort to the patient. Further, because each of the pads can be swiveled out and away from the patient, removal of the patient from the chair is less difficult than it would be if the pads were permanently mounted in fixed supports. Another unique advantage of the present design is that the vertically adjustable back of the chair is attached to the chair frame such that the angle of tilt may be readily adjusted without affecting the posture supports. Also, the chair is constructed so that it can be readily disassembled into four pieces (i.e., the back, two arms and a folding seat/wheel section) without affecting the preset positions of the body support pads. These two features, again, make it very easy to remove a disabled patient from the chair.

The above objects, advantages and distinctions of the present apparatus as well as others will become more apparent upon a reading of the following description in conjunction with a study of the drawings. It is to be recognized though that while the present description is made with respect to a particular and presently preferred embodiment, it may be altered or modified by those of skill in the art without departing from the spirit and scope of the present invention.

SUMMARY OF THE INVENTION

A wheelchair is provided having a plurality of independently adjustable posture support pads for therapeutically supporting the neck, shoulders, trunk and thighs of a seated individual. A yoke-like neck support and right and left shoulder pads are adjustably mounted to the chair's back by support rods and coupling means which permit independent adjustment of each pad along three separate axes to allow for symmetrical and asymmetrical applications. The shoulder pad adjustment assemblies are swivably connected to the back of the chair by spring loaded split-couplers which positively maintain support position, except during seating and unseating. During seating and unseating, the side supports are raised and rotated to one side. The truck support pads are adjustably mounted to brackets secured to each arm of the chair. Adjustment capabilities are provided at the bracket and at the pad itself. Thigh or crotch support is provided via a retractable, adjustable "V" pad assembly that is mounted to the base of the seat. Hip support is provided by right and left trunk support pads that are adjustably retained by support rods to slip coupler means mounted beneath the chair's respective left and right arms.

Also, an inclined adjusting assembly is mounted to the back of the chair for permitting independent adjustment of the back relative to the seat, without affecting the side and neck posture supports. The back and side arm assemblies are also removable by means of associated positive locking couplers.

DESCRIPTION OF THE PREFERRED EMBODIMENT

Figure 1:
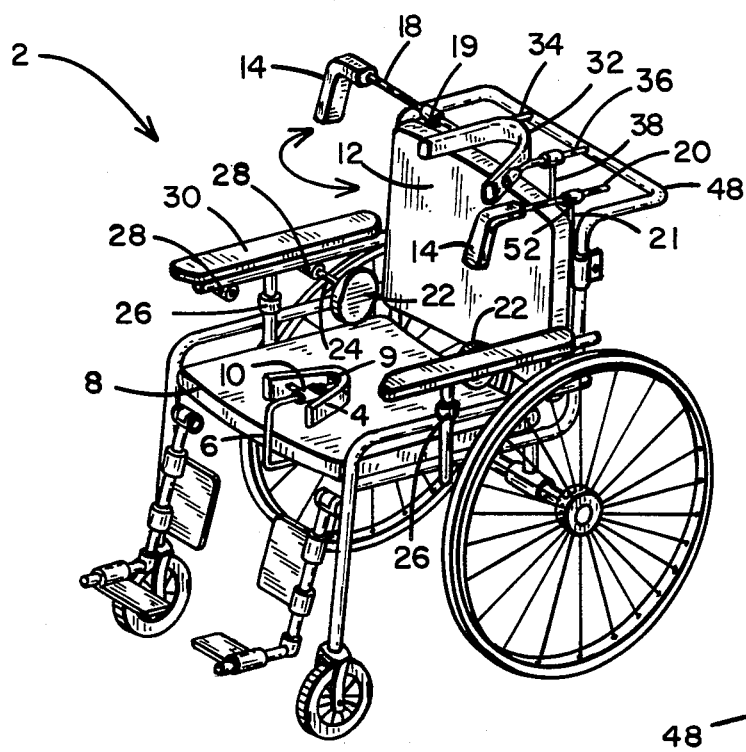
FIG. 1 shows a front perspective view of a typical wheelchair provided with the posture support pads of the present invention.

A generalized perspective view of the presently improved wheelchair is shown in FIG. 1. As can be best seen from FIG. 1, the chair has a frame, four wheels, two leg rests, a seat, right and left arm rests and a back. The chair also includes a plurality of pads or supports to comfortably maintain the proper posture of the patient while seated in the chair. These supports include neck support 32, right and left shoulder support 14, right and left trunk supports 22, and a thigh support 4. Each of these supports are readily adjustable along a plurality of axes. The angular orientation of the back and seat of the chair are also adjustable to promote proper posture and constant comfort. Various modifications have also been made to ease disassembly of the chair's parts to facilitate seating and unseating of the patient as well as storage and transportation of the chair in a motor vehicle.

Figure 5A:
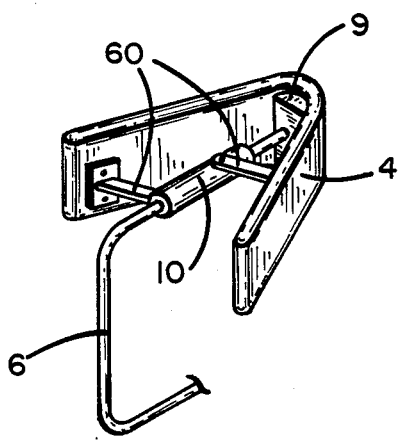
FIG. 5a shows a detailed perspective view of an adjustable thigh pad.
Figure 5B:
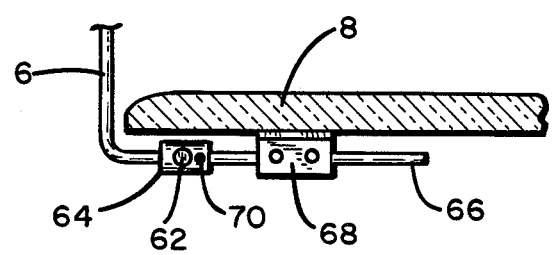
FIG. 5b shows a cross sectional view of a retractable mounting of the thigh pad assembly.

The thigh support 4 commonly known medically as "abductors" or "abduction" and the means by which it is adjustably secured to the seat of the chair are shown in FIGS. 5a and 5b. Thigh support 4 has a generally V-shaped pad member and a half-cylinder shaped member 9 secured to the V-shaped pad member at its apex. Thigh support 4 is held in place by a U-shaped rod 6 which is coupled at one of its ends to cylindrical member 9. The primary purpose of thigh support 4 is to maintain a desired separation between the thighs of a seated patient and to prevent the patient from slouching. Since this desired separation varies from patient to patient, the angular orientation of the two sides of the V-shaped thigh support 4 are adjustable via right and left linkage arms 60. The right and left linkage arms 60 each are respectively secured at one of their ends to the right and left side of the V-shaped support 4. The other end of the right and left linkage arms 60 are rotatably secured to slip coupler 10 which slides along the horizontal portion of the bent support rod 6. By sliding the coupler 10 forward or backward along the support rod 6, the ends of the pad 4 will contract or expand. The desired angular orientation is maintained by tightening set screws (not shown) mounted in the coupler 10.

Shown in FIG. 5b is the assembly which permits adjustment of the position and orientation of thigh support 4. This assembly also permits thigh support 4 to be moved out of the way during seating and unseating of the patient without losing proper adjustment of the thigh support.

The assembly of FIG. 5b is comprised of slip coupler 68, support rod 66, hinge assembly 64 and support rod 6. When properly assembled, slip coupler 68 is secured to the bottom of seat 8 of the chair at approximately its center. Slidably and rotatably received within slip coupler 68 is support rod 66, the forward end of which is welded to rearward end of hinge assembly 64. Also attached to hinge assembly 64, at its forward end, is U-shaped support rod 6. Slip coupler 68 has at least one set screw which can be used to lock rod 66 in place. Hinge assembly 64 has (a) an axle 70 which permits support rods 6 and 66 to rotate with respect to each other about axle 70, and (b) a release pin 62 which can be used to restrict rotational movement of rods 6 and 66 about the axle.

As should be readily apparent to those skilled in the art, the position of thigh pad 4 is adjustable by loosening the set screws of slip coupler 68 and sliding the remainder of the assembly of FIG. 5b forward or backward inside slip coupler 68 until the proper position is achieved. At the same time, the thigh pad assembly may also be selectively rotated as desired about the longitudinal axis defined by the lower portion of rod 6 and rod 66. Once the proper position and orientation have been established the set screws of coupler 68 may be tightened to lock the assembly in place. Those skilled in the art will also recognize that thigh support 4 can readily be moved out of the way during seating and unseating without losing adjustment by activating release pin 62 and rotating support arm 6 and thigh support 4 around axle 70 until thigh support 4 is beneath the chair.

Figure 6A:
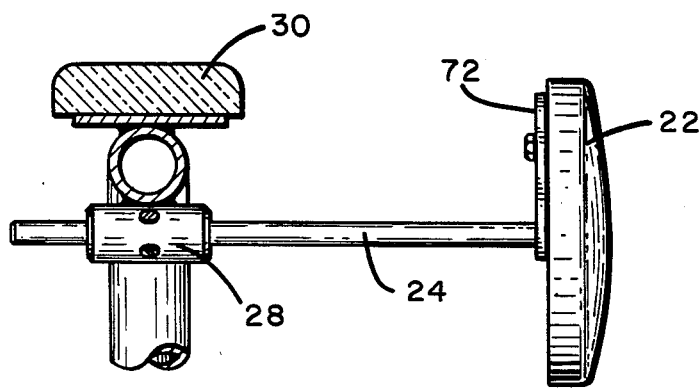
FIG. 6a shows an end view of one of the hip pad assemblies relative to a chair arm.
Figure 6B:
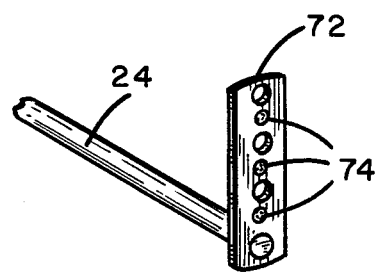
FIG. 6b shows a perspective view of the coupling rods for one of the hip pad supports.

The trunk supports 22 and the means by which they are adjustably secured to the chair are shown in FIGS. 6a and 6b. In the preferred embodiment, separately adjustable right and left trunk supports 22 extend inwardly from beneath the respective vertically adjustable height arms of the chair. Each trunk support 22 has a generally oblong convex pad which contacts the patient.

The pad is constructed of polyurethane material molded about an internal core to which hardware can be fixedly attached. In the preferred embodiment, a plate 72 is attached to the pad using a bolt. As shown in FIG. 6b, plate 72 has a plurality of apertures, dimples 74 projecting from it in the direction of the pad, and a support rod 24 secured to it near one of its ends. Since the plate 72 can be bolted to the pad through any one of the apertures, the degree of eccentricity of the pad with respect to rod 24 is readily modified to provide sufficient adjustability to promote patient posture and comfort. Further, because dimples 74 press into the pad's material, they prevent the pad from rotating with respect to plate 72 and rod 24 and thus help maintain trunk support 22 in proper adjustment when in use.

As best shown in FIG. 6a, support rod 24 is slidably coupled to slip coupler 28 which is welded to the underside of the chair arm 30. Thus, the rods 24 may be extended or retracted and fixed by set screws associated with slip coupler 26.

In passing, it should be further noted that upon disassembly of chair 2, the trunk support pads 22 are not affected in their adjustment since the right and left arms 30 are detachable via inter-locking tubular sections that slide into one another at the slip coupler 26. The ends of the inside tubular sections, in turn, have spring loaded pins (not shown) that lock within mating holes in the stationary tubes so that each arm 30 is released only upon depressing the pin ends and pulling up on the arm 30. It should be noted, too, that an associated, notched bracket is welded to the back of the inside tubular section so as to interlock with a stud mounted on an adjacent tubular member, associated with the seat frame so as to secure the arms 30 against the side forces that are exerted by the hips against the pads 22, then by distributing the forces throughout the chair's frame.

Also present on the wheelchair of the preferred embodiment are a neck support 32 and two shoulder supports 14. These supports and the means by which they are adjustably secured to the wheelchair are shown in FIGS. 2, 3, 4a and 4b.

Figure 2:
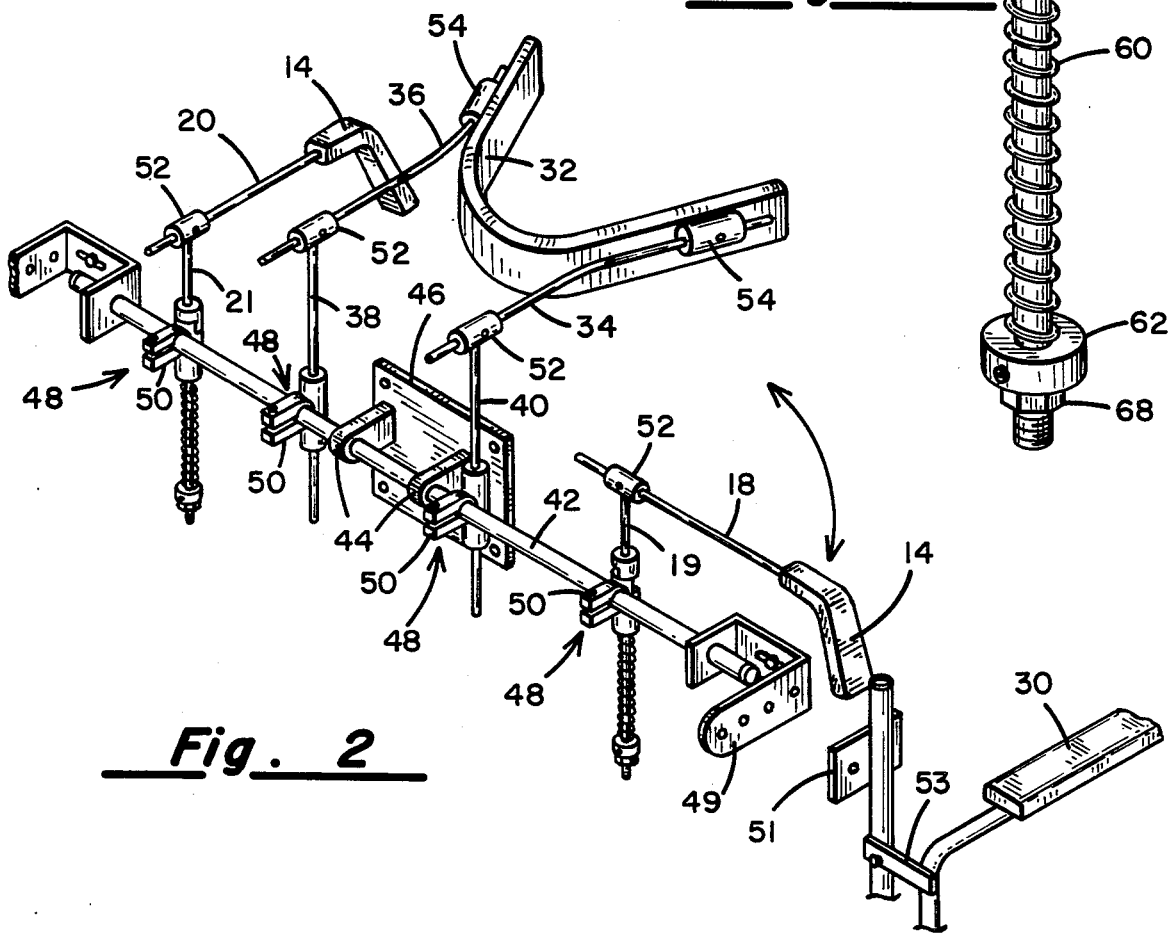
FIG. 2 shows a detailed perspective view of the back assembly and illustrating details of the coupling arrangement for the shoulder and neck supports.

Referring specifically to FIG. 2, shown is a detailed perspective view of the manner of adjusting and coupling the shoulder pads 14 and neck support 32 to the chair back 12. Specifically, each of the pads 14 and 32 are coupled to the chair 2 via a tubular member 42 (typically ⅜ inch stainless steel tubing) which is offset from the back 12 via two standoffs 44 that are welded to a mounting plate 46. Mounting plate 46 is bolted to the back of chair 2. The tubular member 42 is typically sized to be shorter than the distance between the sides of the push bar 48. Also, the means by which member 42 is mounted permit it to be located approximately two inches from the back of the chair.

Also, it should be noted that a multi-operational bracket be coupled to each end of said tubular member 42. Selected apertures thereof are brought into alignment with the apertured member 51 mounted to chair 2 and whereby the inclination of the back 12 can be varied. As mentioned, the notched bracket 53 (only one of which is shown) contains the arm 30 to the chair frame.

Adjustably mounted along the tubular member 42 are a plurality of couplers 48. Each coupler 48 is comprised of a cylindrical slip coupler member, a clamping element 50 welded to the slip coupler and a through bolt. The clamping element 50 and the through bolt are used to secure the coupler 48 to the tubular member 42. Each cylindrical slip coupler section 50 is approximately three inches long and fabricated from ⅝ inch outside diameter tubing having ⅜ inch inside diameter. Allen-type set screws are mounted at 90° relative to one another about the midpoint of each coupler 48.

Secured to the member 42 via couplers 48 are two shoulder supports 14 and neck support 32. Each shoulder support is comprised of a contoured pad, and horizontal support rod 18, a T-shaped slip coupler 52, a vertical support rod 19 which is threaded at one end, a spring 60, a stop member 62 and a nut. When assembled, one end of the horizontal support rod 18 is secured to the contoured pad and is slidably received with slip coupler 52. Extending perpendicularly from rod 18 and fixedly attached to coupler 52 is rod 19. Rod 19 also projects downwardly through slip coupler 48. Spring 60 is positioned so that it surrounds rod 19 in the area between coupler 48 and the bottom of the rod. Stop 62 and nut 48 are secured to rod 19 near its bottom. The bottom of coupler 48 serves as an upper stop for the spring while stop 62 and nut 68 further serving to retain spring 60 in position. A spring clip or the like could, of course, be advantageously employed in place of the nut.

Given the above-described configuration, the distance between the back of the chair and the pad can be adjusted by sliding rod 18 either forwardly or backwardly through coupler 52. Once the proper position has been determined, set screws in coupler 52 can be tightened to lock rod 18 in place. In a similar fashion, the height of the pad can be adjusted by sliding rod 19 up and down within slip coupler 48 and locking rod 19 in place with set screws or the like once the proper adjustment has been determined. Those skilled in the art will further recognize that rods 18 and 19 can be rotated within the slip couplers before tightening the set screws to rotationally adjust the position of the shoulder supports.

Figure 3:
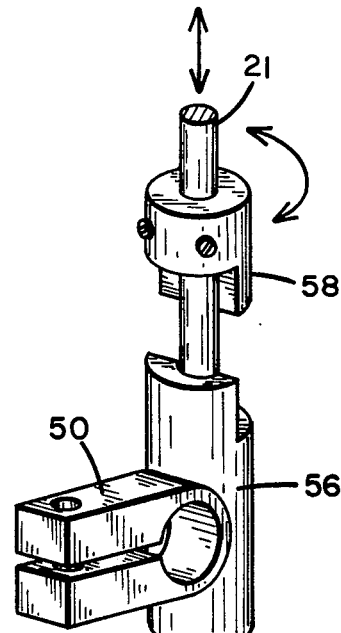
FIG. 3 shows a detailed perspective view of a shoulder pad swival assembly.

Shoulder supports on wheelchairs tend to hinder one's ability to get out of the chair. A significant advantage of the present design is that it permits the shoulder supports 14 to be moved out of the way without taking them out of adjustment. As shown in FIG. 3, couplers 48 can be fabricated in two positions which interlock with one another. In this configuration, clamping element 50 is welded to the lower portion 56 of each coupler 48 and upper position 58 is secured to the support rod 19 via set screws. The force of spring 60 causes the lower and upper portions 56 and 58 of the couplers 48 to interlock.

When seating or unseating an individual, shoulder supports 14 may be lifted until portions 56 and 58 of coupler 48 become disengaged. Once portions 56 and 58 are disengaged, the shoulder supports can be swiveled to the right and left sides of the wheelchair 2 to get them out of the way. The shoulder pads 14 may then be subsequently returned to their normal, preadjusted positions.

While pad 14 is shown with a 90° bend, it is to be recognized that the bend may be adjusted due to fabrication of pad 14 with maleable piece of metal strapping (not shown) therein. Thus, upon bending the pad 14 to a desired angle, the angle will remain upon releasing the pad.

Figure 4A:
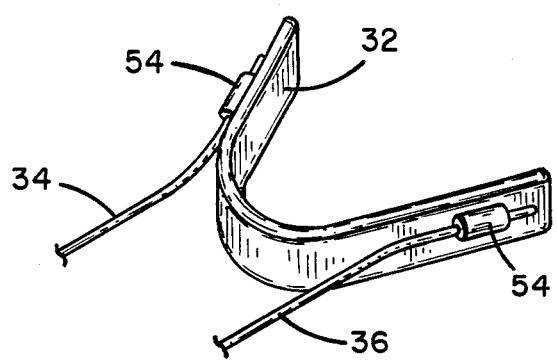
FIG. 4a shows a detailed perspective view of the neck support and its associated slip coupler.
Figure 4B:
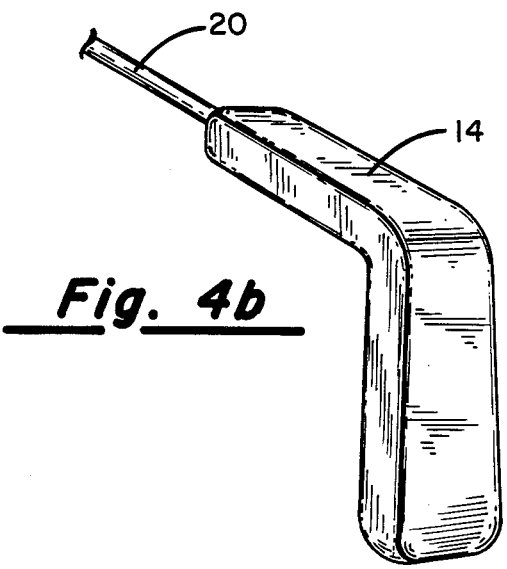
FIG. 4b shows a detailed perspective view of a side support and its associated coupler.

The neck support of the present invention is shown best in FIGS. 2 and 4a. Neck support 32 is comprised of a generally U-shaped pad, a pair of slip couplers 54 each of which are secured to the pad, generally horizontal support rods 34 and 36, a pair of T-shaped slip couplers 52, and vertical support rods 38 and 40. Each of the slip couplers has set screws associated therewith. When assembled, support rods 38 and 40 are each slidably received within a slip coupler 48. Also, the upper ends of rods 38 and 40 are secured to the T-shaped couplers 52. Support rods 34 and 36, which are slightly bent to promote rotational adjustability, are each slidably received within a slip coupler 52 near one end and slip coupler 54 near the other end.

In this configuration, those skilled in the art will recognize that the height of the neck support 32 can be adjusted by sliding support rods 38 and 40 up or down with respect to slip coupler 48. Once the proper height has been established, set screws in the couplers 48 can be used to retain it. Likewise, the angular orientation of neck support 32 and its distance from the back of the chair can be readily adjusted by altering the position of couplers 52 and 54 relative to rods 34 and 36. Set screws are again used to secure the proper adjustment.

As discussed briefly above, the various pads of the present invention can be fabricated of any suitable material. One material found particularly suitable is known as Posturethane ™. While essentially a urethane foam, the present material cures with a relatively thick skin effect and is thus relatively indestructible for those uses to which a wheelchair is normally subjected. Previously though, one of the most common problems with wheelchairs was the wearability of the vinyl covers that were employed. This, however, is not a problem with the Posturethane TM and which may easily be cleaned with most available cleaners and which also does not readily tear or puncture due to the thick skin.

From the above, it should be apparent that the present wheelchair incorporates a number of new improved features which, in total, provide for a wheelchair that therapeutically accommodates a broad range of users. The chair is easily cared for, is easily disassembled and transported and provides heretofore unavailable posture support for those users affected by debilitating diseases, such as scoliosis or the like.

While the present invention has been described with respect to its presently preferred embodiment, it is to be recognized that various modifications or alterations may suggest themselves to those of skill in the art without departing from the spirit and scope of the present invention as claimed hereinafter. It is, therefore, contemplated that the following claims will be interpreted so as to encompass all equivalent structures within the spirit and scope thereof.

What is claimed is:

1. Posture support apparatus comprising in combination:
    a wheelchair in which an individual can be seated having a frame, a seat, a back, and two arms;
    a plurality of adjustable support means attached to the chair for therapeutically supporting said individual in a select posture, an adjustment means associated with each support means for adjusting the position and angular orientation of its associated support means with respect to said wheelchair, moving means for moving at least one of said support means with respect to said wheelchair and independently of its associated adjustment means, to facilitate seating or unseating of the individual in the chair without disturbing the setting of said associated adjustment means; and
    wherein one of said adjustable support means includes a leg support means for separating the thighs of the individual.

2. The apparatus of claim 1 wherein said leg support means includes:
    a V-shaped pad, convergent toward said back, for contacting the thighs of said individual; and
    wherein a first one of said adjustment means associated with said leg support means includes means for adjusting the angular orientation of the sides of the V-shaped pad; and a U-shaped rod supporting said pad and a coupler supporting said U-shaped rod slidably relative to said chair for increasing and decreasing the distance of the V-shaped pad from the back of the chair.

3. The apparatus of claim 2 wherein a first one of said moving means, associated with said leg support means, includes:
    an axle which permits rotation of the U-shaped rod between a first position in which the V-shaped pad is in proper adjustment above the seat of the chair for supporting the individual, and a second position wherein the V-shaped pad is located beneath the chair seat; and
    releasable locking means for preventing rotation between said first and second position except when such rotation is desired.

4. The apparatus of claim 1 wherein a second one of said support means includes trunk support means for retaining the trunk of the individual in a select position.

5. The apparatus of claim 4 wherein said trunk support means includes:
    at least one trunk support pad for contacting the individual's hip area; a bracket secured to said trunk support pad; and
    wherein a second one of said adjustment means, associated with said trunk support means, includes a trunk support rod attached to and extending generally perpendicularly from said bracket; trunk support rod connector means attached to an associated arm of the chair slidably supporting said trunk support rod; and means for locking said trunk support rod with respect to said connector means.

6. The apparatus of claim 5 wherein said second adjustment means further includes:
    a plurality of openings in said bracket for receiving a bolt for securing said bracket to said trunk support pad so that the degree of eccentricity of the trunk support pad with respect to the rod can be adjusted; and a series of dimples on said bracket projecting toward the trunk support pad for preventing rotation of the pad with respect to the bracket.

7. The apparatus of claim 5 further including a second one of said moving means, associated with said trunk support means, comprising means for disconnecting said associated arm from the chair during seating and unseating of the individual.

8. The apparatus of claim 1 wherein a third one of said adjustable support means includes a shoulder support means for retaining the shoulders of the individual in a select position.

9. The apparatus of claim 8 wherein said shoulder support means includes:
    a contoured shoulder pad; and wherein a third one of said adjustment means includes a generally horizontal shoulder support rod secured at one of its ends to said contoured shoulder pad; T-shaped first shoulder coupler means slidably and rotatably supporting said generally horizontal shoulder support rod and secured to a generally vertical shoulder support rod; second shoulder coupler means slidably and rotatably supporting said vertical shoulder support rod with respect to the chair; and locking means associated with said first and second shoulder coupler means for locking said shoulder support rods with respect to said chair.

10. The apparatus of claim 9 wherein said second shoulder coupler means is comprised of first and second interacting members, said first interacting member being in fixed relation with respect to the chair and slidably supporting said vertical shoulder support rod, and said second interacting member is slidable relative to said vertical shoulder support rod to enable its selective positioning on said vertical rod, said locking means fixing said second interacting member on said vertical support rod after said selective positioning; said first and second interacting members movable into and out of interlocking engagement to provide a third one of said moving means, associated with said shoulder support means.

11. The apparatus of claim 10 further including:
    a spring surrounding a portion of said vertical shoulder support rod beneath said second shoulder coupler means; and an adjustable stop means located on said vertical shoulder support rod beneath said spring for retaining said spring.

12. The apparatus of claim 10 wherein said contoured shoulder pad is comprised of a flexible plate which can be easily bent to a desired shape and will retain said shape, and a covering over said plate.

13. The apparatus of claim 1 wherein a fourth one of said support means includes a neck support comprised of:

a contoured neck pad having a general U-shape; and wherein a fourth one of said adjustment means includes a first neck connector means secured to the outside surface of said neck pad near each of its ends; a horizontal neck support rod in slidable engagement with each first neck connector means; a second T-shaped neck connector means in slidable engagement with each horizontal neck support rod; a vertical neck support rod secured at one of its ends to each second T-shaped neck connector means; a third neck connector means slidably supporting each vertical neck support rod and in fixed relation to said chair; and means associated with said neck connector means for locking said vertical and horizontal neck support rods relative to the chair.

* * * * *